United States Patent [19]

Manning

[11] 3,974,283

[45] Aug. 10, 1976

[54] N-SUBSTITUTED-4-t-BUTYL-1-PYRIDINETHIOCARBOXAMIDES AND THEIR USE FOR TREATMENT OF INFLAMMATION OR PAIN

[75] Inventor: Robert E. Manning, Mountain Lakes, N.J.

[73] Assignee: Sandoz, Inc., E. Hanover, N.J.

[22] Filed: June 19, 1975

[21] Appl. No.: 588,249

Related U.S. Application Data

[63] Continuation of Ser. No. 452,189, March 18, 1974, abandoned, which is a continuation of Ser. No. 321,234, Jan. 5, 1973, abandoned.

[52] U.S. Cl. ........................ 424/263; 260/294.8 E
[51] Int. Cl.² ................ A01N 9/22; C07D 213/83

[58] Field of Search ............... 260/294.8 E 424/263

[56] References Cited
UNITED STATES PATENTS 3,825,547  7/1974  Loev ........................ 260/294.8 E

*Primary Examiner*—Alan L. Rotman
*Attorney, Agent, or Firm*—Gerald D. Sharkin; Robert S. Honor

[57] ABSTRACT

N-substituted-4-t-butyl-1-pyridinethiocarboxamides, e.g. N-methyl-4-t-1,2,3,6-tetrahydro-1-pyridinethiocarboxamides, are prepared by treating 4-t-butyl-1,2,3,6-tetrahydropyridine with a substituted isothiocyanate and are useful as anti-inflammatory and non-narcotic analgesic agents.

11 Claims, No Drawings

N-SUBSTITUTED-4-t-BUTYL-1-PYRIDINETHIOCARBOXAMIDES AND THEIR USE FOR TREATMENT OF INFLAMMATION OR PAIN

This application is a continuation of application Ser. No. 452,189 filed Mar. 18, 1974, now abandoned, which in turn is a continuation of application Ser. No. 321,234 filed Jan. 5, 1973, now abandoned.

This invention relates to N-substituted-4-t-butyl-1-pyridinethiocarboxamides; which exhibit anti-inflammatory and non-narcotic analgesic activity. In particular, it relates to N-substituted-4-t-butyl-1,2,3,6-tetrahydro-pyridinethiocarboxamides, pharmaceutically acceptable salts thereof, their preparation and intermediates therefor.

The compounds of this invention may be represented by the formula

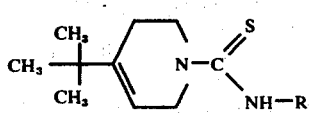

where R represents lower alkyl, i.e. alkyl having 1 to 4 carbon atoms, e.g., methyl, ethyl, isopropyl and the like, or lower alkenyl, i.e. alkenyl having 3 to 5 carbon atoms, e.g. allyl, methallyl and the like, and pharmaceutically acceptable acid addition salts thereof.

The compounds of formula (I) are prepared according to the following reaction scheme:

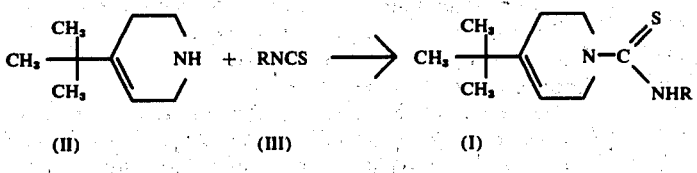

where R is as defined above.

The compounds of formula (I) are prepared by treating a compound of formula (II) with an isothiocyanate of formula (III) in a non-hydroxylic inert solvent. Although the particular non-hydroxylic solvent used is not critical, the aromatic hydrocarbons such as benzene, toluene, and the like and ethers such as diethylether, dioxane or tetrahydrofuran may be employed, the latter being especially preferred. The temperature of the reaction is not critical, but it is preferred that the process be carried out at temperatures between about 0° to 100°C. especially from about 20° to 50°C. Although the reaction time is not critical, it is preferred that the reaction be run from about 1 to 30 hours, more preferably from about 15 to 24 hours. The compounds of formula (I) may be recovered using conventional techniques such as evaporation.

The compounds of formulae (II) and (III) are known and may be prepared by methods disclosed in the art from known starting materials.

The compounds of formula (I) are useful because they possess pharmacological activity in animals. In particular, the compounds of formula (I) are useful as anti-inflammatory agents, as indicated by their activity in rats dosed orally with 25 to 105 mg./kg. of test compound using the acute carrageenan-induced edema procedure substantially as described by Winter (Proc. Soc. Exptl. Biol., 111:544, 1962) and as indicated by plethysmographic measurement of food volumes on mature Lewis Strain rats made arthritic by a single 0.1 ml. injection of complete Freunds Adjuvant and dosed orally for 14 days with the compound of formula (I) at a daily dosage rate of 25–50 mg./kg.

The compounds of formula (I) are also useful because they exhibit non-narcotic analgesic activity as indicated by their activity in rat dosed orally with 5 to 40 mg./kg. of the compound. The analgesic activity is measured by the application of pressure to the yeast-inflamed foot of a rat substantially as described by L. O. Randall and J. J. Selitto (Arch. Int. Pharmacodyn. 111:409, 1957) as modified by C. A. Winter and L. Flatalic (J.P.E.T. 148:373, 1965).

For both usages, the compounds of formula (I) may be combined with a pharmaceutically carrier or adjuvant, and may be administered orally in such forms as tablets, capsules, elixers, suspensions and the like, or parenterally in the form of an injectable solution or suspension.

Furthermore, the compounds of formula (I) may be similarly administered in the form of their non-toxic pharmaceutically acceptable acid addition salts. Such salts possess the same order of activity as the free base, and are readily prepared by reacting the base with an appropriate acid and accordingly are included within the scope of the invention. Representative of the acid addition salts are the mineral acid salts, such as the hydrochloride, hydrobromide, sulfate, phosphate and the like and the organic acid salts, such as the succinate, benzoate, acetate, p-toluenesulfonate, benzenesulfonate, and the like.

For both of the above-mentioned uses, the effective dosage of the compounds of formula (I) will depend on the particular compound employed, the method of administration and the severity of the condition being treated. In general, satisfactory results are obtained when these compounds are administered in the treatment of either inflammation or analgesia, or both at a daily dosage of about 1 milligram to about 200 milligrams per kilogram of animal body weight, preferably orally. This daily dosage is preferably administered 2 to 4 times a day, or in sustained release form. For most large mammals, such as primates, the total daily dosage is from about 75 milligrams to about 2,000 milligrams. Dosage forms suitable for internal use comprise from about 20 milligrams to about 1000 milligrams of the active compound in intimate admixture with a solid or liquid pharmaceutically acceptable carrier or diluent.

A representative formulation suitable for oral administration two to four times a day in the treatment of inflammation and analgesia is a capsule prepared by standare encapsulating techniques which contains the following:

| Ingredients | Weight (mg.) |
|---|---|
| N-methyl-4-t-butyl-1,2,3,6-tetrahydro-pyridine- | |

| Ingredients | Weight (mg.) |
|---|---|
| thiocarboxamide | 100 |
| Inert solid diluent (starch, lactoce, kaolin) | 200 |

EXAMPLE 1

N-methyl-4-t-butyl-1,2,3,6-tetrahydro-1-pyridinethiocarboxamide

In 60 ml. of anhydrous tetrahydrofuran, there is dissolved 12.0 grams of 4-t-butyl-1,2,3,6-tetrahydropyridine. Stirring is initiated and there is added 7.3 grams of methylisothiocyanate in 25 ml. of anhydrous tetrahydrofuran. After stirring the reaction mixture for 18 hours at room temperature, the tetrahydrofuran is evaporated in vacuo at 50°C/20 mmHg. The resulting oil is crystallized from methylene chloride/pentane 1:1 to give N-methyl-4-t-butyl-1,2,3,6-tetrahydro-1-pyridinethiocarboxamide; m.p. 76° to 78°C.

The product N-methyl-4-t-butyl-1,2,3,6-tetrahydro-1-pyridinethiocarboxamide is an effective anti-inflammatory and non-narcotic analgesic agent when orally administered to animals suffering from inflammation and/or analgesia at a dosage from 50 to 250 mg. four times per day.

EXAMPLE 2

N-ethyl-4-t-butyl-1,2,3,6-tetrahydro-1-pyridinethiocarboxamide

In 20 ml. of anhydrous tetrahydrofuran there is dissolved 5.0 grams of 4-t-butyl-1,2,3,6-tetrahydropyridine. Stirring is initiated and there is added 3.14 grams of ethylisothiocyanate in 10 ml. of anhydrous tetrahydrofuran allowing the reaction to run at room temperature. After stirring the reaction mixture for 18 hours, the tetrahydrofuran is evaporated in vacuo to give N-ethyl-4-t-butyl-1,2,3,6-tetrahydro-1-pyridinethiocarboxamide.

EXAMPLE 3

N-allyl-4-t-butyl-1,2,3,6-tetrahydro-1-pyridinethiocarboxamide

In 20 ml. of anhydrous tetrahydrofuran there is dissolved 5.0 grams of 4-t-butyl-1,2,3,6-tetrahydropyridine, and with stirring there is added 3.5 grams of allylisothiocyanate in 10 ml of anhydrous tetrahydrofuran. The reaction mixture is stirred for 24 hours at room temperature and the tetrahydrofuran is evaporated in vacuo. The resulting solid is dried at 50°C/20 mmHg. to remove any unreacted allylisothiocyanate to give N-allyl-4-t-butyl-1,2,3,6-tetrahydro-1-pyridinethiocarboxamide.

What is claimed is:

1. A compound of the formula

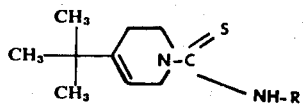

where R represents lower alkyl or lower alkenyl.

2. A pharmaceutically acceptable acid addition salt of a compound of claim 1.

3. A compound of claim 1 in which R represents lower alkyl.

4. A compound of claim 1 in which R represents lower alkenyl.

5. A compound of claim 1 in which R represents methyl, ethyl, or allyl.

6. The compound of claim 1 which is N-methyl-4-t-butyl-1,2,3,6-tetrahydro-1-pyridinethiocarboxamide.

7. The compound of claim 1 which is N-ethyl-4-t-butyl-1,2,3,6-tetrahydro-1-pyridinethiocarboxamide.

8. The compound of claim 1 which is N-allyl-4-t-butyl-1,2,3,6-tetrahydro-1-pyridinethiocarboxamide.

9. A pharmaceutical composition for use in the treatment of inflammation or pain which comprises an anti-inflammatory or analgesic effective amount of a compound of claim 1 and a pharmaceutically acceptable inert diluent or carrier therefor.

10. The method of treating inflammation which comprises orally or parenterally administering to a mammal in need of said treatment an anti-inflammatory effective amount of a compound of claim 1.

11. The method of treating pain which comprises orally or parenterally administering to a mammal in need of said treatment an non-narcotic analgesic effective amount of a compound of claim 1.

* * * * *